United States Patent
Shieh et al.

(10) Patent No.: US 8,673,358 B2
(45) Date of Patent: Mar. 18, 2014

(54) NANO-CARRIER, COMPLEX OF ANTICANCER DRUG AND NANO-CARRIER, PHARMACEUTICAL COMPOSITION THEREOF, METHOD FOR MANUFACTURING THE COMPLEX, AND METHOD FOR TREATING CANCER BY USING THE PHARMACEUTICAL COMPOSITION

(75) Inventors: Dar-Bin Shieh, Tainan (TW); Chen-Sheng Yeh, Tainan (TW); Dong-Hwang Chen, Tainan (TW); Ya-Na Wu, Tainan (TW); Ping-Ching Wu, Kaohsiung (TW)

(73) Assignee: National Cheng Kung University, Tainan (TW)

( * ) Notice: Subject to any disclaimer, the term of this patent is extended or adjusted under 35 U.S.C. 154(b) by 491 days.

(21) Appl. No.: 12/805,424

(22) Filed: Jul. 30, 2010

(65) Prior Publication Data
US 2012/0027861 A1 Feb. 2, 2012

(51) Int. Cl.
*A61K 9/16* (2006.01)
*A61K 9/50* (2006.01)

(52) U.S. Cl.
USPC ...................................................... 424/490

(58) Field of Classification Search
None
See application file for complete search history.

(56) References Cited

U.S. PATENT DOCUMENTS 7,259,252 B2 * 8/2007 Mirkin et al. ................ 536/23.1
2002/0137071 A1 * 9/2002 Mirkin et al. ..................... 435/6

OTHER PUBLICATIONS

Tim Mosmann; Rapid Colorimetric Assay for Cellular Growth and Survival: Application to Proliferation and Cytotoxicity Assays; *Journal of Immunological Methods,* Jun. 20, 1983; p. 55-p. 63; vol. 65; U.S.A.
Engin Ulukaya, et al.; Interference by Anti-Cancer Chemotherapeutic Agents in the MTT-Tumor Chemosensitivity Assay; *Experimental Chemotherapy,* Jun. 13, 2003; p. 43-p. 50; Karger AG, Basel.
Ching-Ming Wu, et al.; Synthesis of Polynucleotide Modified Gold Nanoparticles as a High Potent Anti-Cancer Drug Carrier; *Journal of the Chinese Chemical Society,* Aug. 1, 2009; p. 703-p. 708; vol. 56; No. 4.

* cited by examiner

*Primary Examiner* — Robert M Kelly
(74) *Attorney, Agent, or Firm* — Bacon & Thomas, PLLC

(57) ABSTRACT

The present invention relates to a nano-carrier for an anticancer drug, which comprises: a metal nanoparticle; and a polynucleotide for connecting with an anticancer drug having a pyrimidine group or a purine group, wherein the polynucleotide connects to a surface of the metal nanoparticle, and the anticancer drug binds to the polynucleotide through the pyrimidine group or the purine group. In addition, the present invention also provides a complex of an anticancer drug and a nano-carrier, a pharmaceutical composition thereof, a method for manufacturing the complex, and a method for treating a cancer by using the pharmaceutical composition.

6 Claims, 2 Drawing Sheets

NANO-CARRIER, COMPLEX OF ANTICANCER DRUG AND NANO-CARRIER, PHARMACEUTICAL COMPOSITION THEREOF, METHOD FOR MANUFACTURING THE COMPLEX, AND METHOD FOR TREATING CANCER BY USING THE PHARMACEUTICAL COMPOSITION

BACKGROUND OF THE INVENTION

1. Field of the Invention

The present invention relates to a nano-carrier, a complex of an anticancer drug and a nano-carrier, a pharmaceutical composition thereof, a method for manufacturing the complex, and a method for treating a cancer by using the pharmaceutical composition and, more particularly, to a nano-carrier which is able to carry an anticancer drug and release the anticancer drug near the location of cancer cells, a complex of an anticancer drug and a nano-carrier, a pharmaceutical composition thereof, a method for manufacturing the complex, and a method for treating a cancer by using the pharmaceutical composition 2. Description of Related Art Chemotherapeutic agents are cytotoxic drugs that usually target fast growing cells through blockage of critical pathways for cell division as well as promoting apoptosis. One kind of the widely used chemotherapeutic agents serving as anti-virus and/or anti-cancer drugs is nucleotide-like compounds. The nucleotide-like compounds can kill the virus-infected cells and/or cancer cells or inhibit the growth thereof through interfering with the nucleic acid metabolisms and cell divisions, and promoting apoptosis. However, the nucleotide-like compounds are also cytotoxic to normal cells, so some side effects and complications may occur during the administration of these compounds, and the dosages thereof must be limited. Also, some nucleotide-like compounds may interfere with the gene replication and transcription in mitochondrions and cell nucleuses when these compounds are administered over a long period of time. Hence, some side effects, such as mitochondrial disorder and bone marrow suppression, may occur in the patients taking these compounds for a long time.

In the clinical researches, it is found that when the nucleotide-like compounds are used in the anti-virus therapy, drug-resistant strains of virus may exist in some patients taking drugs with a single-agent for a long time. Hence, the activity of the virus in serum increases again, the patient's condition gets worse, and the drugs have to be replaced by a new agent. In addition, when the nucleotide-like compounds used as an anti-cancer drug are administered for a long time, cancer cells with drug-resistant strains may be generated and cause the efficacy of the chemical therapy to decrease. Furthermore, the nucleotide-like compounds attack both normal and cancerous cells thereby often resulting in significant side effects, notably lethal cardiac toxicity. Hence, the dose of the anti-cancer drug must be limited to prevent side effects.

Fluorouracil (5-FU) is one kind of nucleotide-like compounds, which is the main ingredient for treating GI tract cancers, including colorectal, stomach, and oral cancers in the past decades. 5-FU is a pyrimidine analogue and can be converted in the cancer cell to form cytotoxicity metabolites, which then become incorporated into DNA and RNA. The compounds eventually induce cell cycle arrest and apoptosis by inhibiting DNA synthesis.

Therefore, it is desirable to provide an anti-cancer drug, and the drug release strategies thereof can be controlled and sustained to increase local concentration of anti-cancer drugs, in order to decrease potential side effects.

SUMMARY OF THE INVENTION

The object of the present invention is to provide a nano-carrier for an anticancer drug, a complex of an anticancer drug and a nano-carrier, a pharmaceutical composition for treating a cancer, which have the properties of the controlled drug release and can be used to treat cancer cell localizedly.

Another object of the present invention is to provide a method of manufacturing a complex of an anticancer drug and a nano-carrier, which can be used to prepare a complex with the property of controlled drug release.

A further object of the present invention is to provide a method of treating a cancer, which can be used to localizedly treat cancer cells in patients.

To achieve the object, the nano-carrier for an anticancer drug of the present invention comprises: a metal nanoparticle; and a polynucleotide for connecting with an anticancer drug having a pyrimidine group or a purine group, wherein the polynucleotide connects to a surface of the metal nanoparticle, and the anticancer drug binds to the polynucleotide through the pyrimidine group or the purine group.

In addition, the complex of an anticancer drug and a nano-carrier of the present invention comprises: a nano-carrier comprising a metal nanoparticle, and a polynucleotide connecting to a surface of the metal nanoparticle; and an anticancer drug with a pyrimidine group or a purine group, wherein the anticancer drug binds to the polynucleotide through the pyrimidine group or the purine group.

The present invention also provides a pharmaceutical composition for treating a cancer, which comprises the aforementioned complex of an anticancer drug and a nano-carrier.

Further, the method of manufacturing a complex of an anticancer drug and a nano-carrier of the present invention comprises the following steps: (A) providing a nano-carrier, and an anticancer drug, wherein the nano-carrier comprises a metal nanoparticle, and a polynucleotide connecting to a surface of the metal nanoparticle, and the anticancer drug comprises a pyrimidine group or a purine group; and (B) mixing the anticancer drug with the nano-carrier to obtain a complex of the anticancer drug and the nano-carrier, wherein the anticancer drug binds to the polynucleotide through the pyrimidine group or the purine group.

In addition, the method for treating a cancer of the present invention comprises: providing the aforementioned pharmaceutical composition to a patient.

According to the nano-carrier, the complex of an anticancer drug and the nano-carrier, and a pharmaceutical composition thereof of the present invention, to the nano-carrier can carry anticancer drug and release the anticancer drug near the location of cancer cells. In the present invention, the base group of the polynucleotide is complementary to the pyrimidine group or the purine group anticancer drug, so the nano-carrier of the present invention can carry the anticancer drug. Furthermore, the polynucleotide can serve as a natural biopolymer and decrease the potential toxicity, metabolic clearance and immunological issues. In addition, polynucleotide such as anti-sense oligonucleotide can be applied for the modulation of gene expression. By modification of the polynucleotide sequence used, it is possible to carry different anticancer drugs, and achieve the purposes of integrated gene expressive modification and controlled drug release. Because the anticancer drug can be released localizedly, it is possible to prevent the anticancer drug from attacking the normal cells and reduce the generation of the drug resistance.

According to the present invention, one end of the polynucleotide connects to the surface of the metal nanoparticle. Herein, the polynucleotide may is connected to the surface of the metal nanoparticle through a covalent bonding or an affinity adsorption.

According to the present invention, the material of the metal nanoparticle may be any biocompatible material. Preferably, the metal nanoparticle is an Au nanoparticle, or a nanoparticle (for example, an Fe core) coated with an Au shell. More preferably, the metal nanoparticle is an Au nanoparticle. In addition, the shape of the metal nanoparticle is not particularly limited. Preferably, the metal nanoparticle is spherical.

Furthermore, according to the present invention, the metal nanoparticle is nano-sized. Preferably, the diameter of the metal nanoparticle is 1-100 nm. More preferably, the diameter of the metal nanoparticle is 1-50 nm. Most preferably, the diameter of the metal nanoparticle is 1-30 nm.

According to the present invention, the sequence of the polynucleotide may be designed according to the anticancer drug. Preferably, the polynucleotide comprises at least one adenine. When the polynucleotide comprises adenine, an anticancer drug named Fluorouracil (5-FU) can bond to the polynucleotide through the pyrimidine group of 5-FU. Therefore, the complex of the 5-FU and the nano-carrier can be used to treat GI tract cancer, and is especially used in chemotherapy for colorectal cancers.

DETAILED DESCRIPTION OF THE PREFERRED EMBODIMENT

Figure 1:
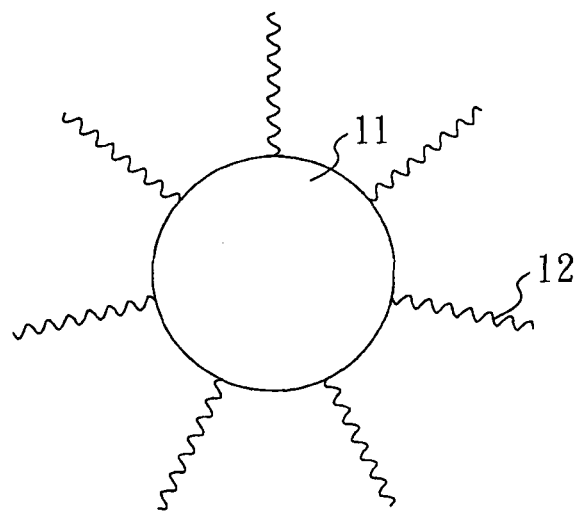
FIG. 1 is a perspective view of a nano-carrier for an anticancer drug of the present invention.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

Preparation of Au Nanoparticles

Au nanoparticles are reduced from Au salts and prepared through a conventional chemical co-precipitation process. The brief process for preparing Au nanoparticles is illustrated as follow.

50 mL of 38.8 mM trisodium citrate (Sigma Aldrich Inc., USA) solution was added to a boiling $HAuCl_4$ solution (1 mM, 500 mL), and the color of the resulted solution is yellow. When the original yellow color turned into a burgundy-wine red, the solution was slowly cooled to room temperature, and Au nanoparticles coated with citrate are obtained.

Then, a UV-vis spectrophotometer (NanoDrop™ 1000, NanoDrop Technologies, LLC, USA) was used to measure the adsorption spectra of the obtained Au nanoparticles. TEM and photon correlation spectroscopy (Delsa™ Nano Zeta Potential and Submicron Particle Size Analyzer, Beckman Coulter, Inc. USA) was applied to measure their conformation and distributions of the particle size and the hydrodynamic size.

The absorption spectrum shows that the obtained Au nanoparticles have a characteristic optical absorption peak at 520 nm. In addition, the results of the TEM and the photon correlation spectrum show that the obtained Au nanoparticles have diameters of 12 nm. The mean hydrodynamic size of the Au particles is 25 nm. The Zeta potential (surface charge) of the Au particles is at −9.58±1.68 mV.

Preparation of a Nano-Carrier for an Anticancer Drug

The poly-A polynucleotide (30 base pairs) with alkane thiol modified 5' termini (MDBio Inc, Taipei, Taiwan) was dissolved in $ddH_2O$. For the conjugation of the poly-A polynucleotide to the Au nanoparticles, 20 µl, of Au colloids (60 nM) was incubated with 34 µL of poly-A polynucleotides (100 µM) for 24 hrs. The reaction mixture was then added with NaCl solution to a final concentration of 0.05 M, then incubated for 24 hrs at 4° C. The salt concentration was gradually increased to 0.1 M then 2 M for the incorporation of more poly-A polynucleotides on the surfaces of the Au nanoparticles in the following two runs of 8 hrs incubation period. The solution was then centrifuged at 10,000×g for 10 min and the pellet was collected, washed three times with Phosphate Buffered Saline (PBS), and finally dissolved in PBS.

After the aforementioned process, a nano-carrier for an anticancer drug was obtained, which comprises: a metal nanoparticle 11 (Au nanoparticle); and a polynucleotide 12 (poly-A polynucleotides) for connecting with an anticancer drug, wherein the polynucleotide connects to a surface of the metal nanoparticle, as shown in FIG. 1.

The UV-vis spectrophotometer, TEM and photon correlation spectroscopy are also applied to measure the obtained nano-carrier. The absorption spectrum shows that the nano-carrier has a characteristic optical adsorption peak at 525 nm. The mean hydrodynamic size of the nano-carrier is 34 nm. The surface charge of the nano-carrier is −18.19±1.23 mV due to decoration of the negatively charged poly-A polynucleotide.

Preparation of a Complex of an Anticancer Drug and a Nano-Carrier

A stock solution of Fluorouracil (5-FU) (100 mg/mL) in PBS was provided. The formula of the 5-FU is presented as the following formula (I).

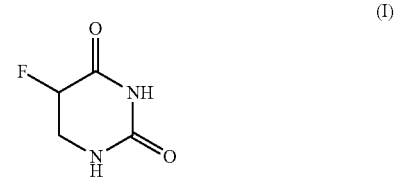

(I)

Then, the solution of the 5-FU was added to the aforementioned solution of the nano-carriers (pH 7.0, in PBS) to a final concentration of 10 mg/mL, and then incubated for 24 hrs. Finally, a complex of an anticancer drug (5-FU) and a nano-carrier is obtained, which comprises: a nano-carrier comprising an Au nanoparticle, and poly-A polynucleotides is connected to the surface of the Au nanoparticle; and 5-FU with a pyrimidine group, wherein the 5-FU binds to the poly-A polynucleotides through the pyrimidine group.

The hydrodynamic size of the complex is 35 nm, and the surface charge is −21.66±2.19 mV. In addition, the absorption spectrum of the complex shows that two characteristic optical absorption peaks respectively at 299 nm and 525 nm, wherein 299 nm is the characteristic optical absorption peak of 5-FU, and 525 nm is the characteristic optical adsorption peak of the nano-carrier. This result suggests a successful loading of 5-FU onto the nano-carrier.

Measuring the Anti-Drug Loaded on the Complex

UV-vis spectrophotometric analysis revealed a specific adsorption peak of 5-FU at 299 nm and a linear association between $OD_{299}$ and 5-FU concentrations. Au nanoparticles without polynucleotides conjugation served as the control. The amount of 5-FU in the remaining supernatant was measured by spectrophotometer to estimate the amount of drugs loaded onto the nanoparticles. Drug loading (%) efficiency was calculated as [$OD_{299}$ of the original solution (10 mg/mL 5-FU)–$OD_{299}$ of the supernatant after drug loading]/[$OD_{299}$ of the original solution (10 mg/mL 5-FU)]×100.

Figure 2:
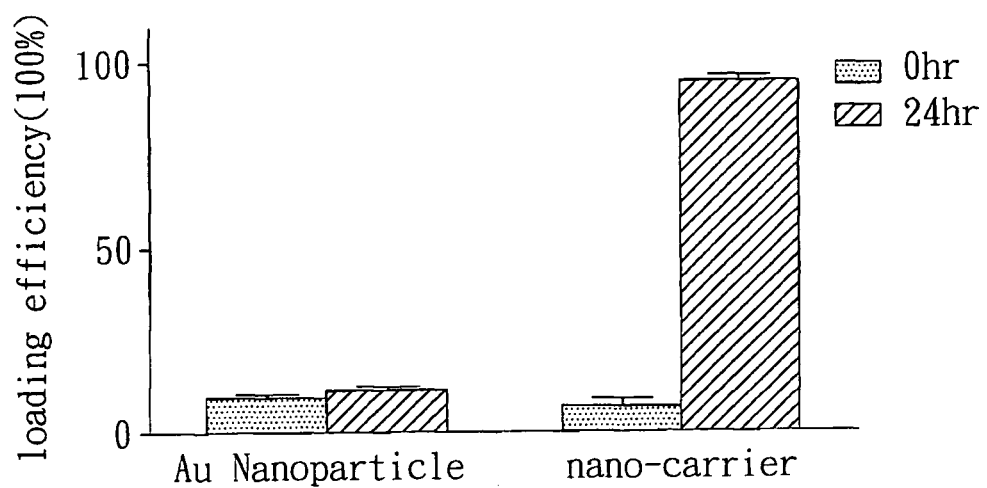
FIG. 2 is a diagram showing the drug loading efficiency of Au nanoparticles and nano-carriers for an anticancer drug of the present invnetion.

The result of the drug loading efficiency is shown in FIG. 2. The results indicated that Au nanoparticles absorbed only 10% of 5-FU in PBS. On the other hand, nano-carrier absorbed about 96% 5-FU after 24 hrs. This result shows that the nano-carrier of the present invention is a high capacity anticancer drug carrier.

Evaluation of the Drug Release from the Nano-Carrier

The drug releasing kinetics of the nano-carrier was evaluated at different pH environment (pH=5, 7, 9) in a PBS buffer in 0.5, 1, 3, 6, 12, 24 and 48 hrs at 37° C. The drug-releasing rate was calculated as: % drug release=[$OD_{299}$ of the supernatant at each time/$OD_{299}$ of the original loaded drugs on the Au-polynucleotide complex]×100. The absorbance of the PBS buffer without drug ($OD_{299}$) was used as a blank, and each absorbance was subtracted with blank.

Figure 3:
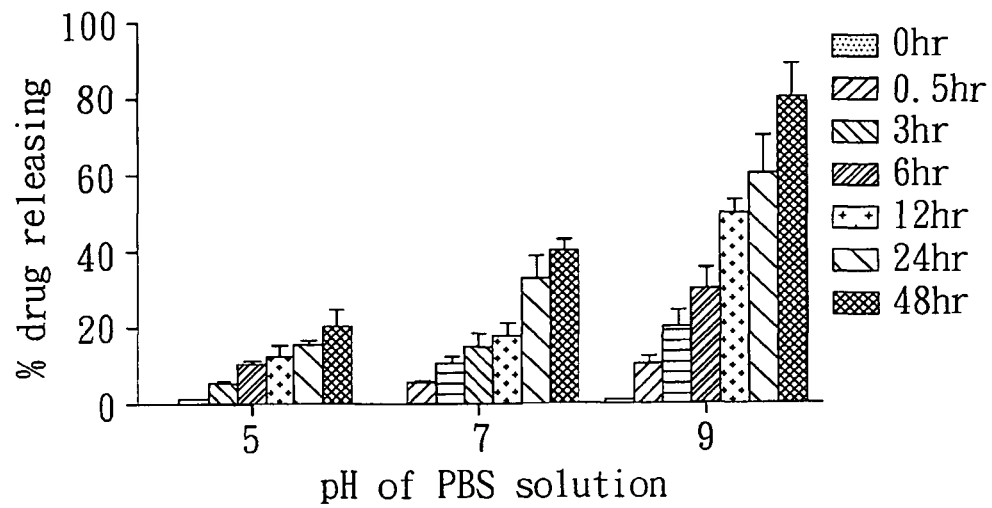
FIG. 3 is a diagram showing the drug releasing rate of 5-FU from nano-carriers of the present invention in a PBS solution with different pH.

The result of the drug-releasing rate is shown in FIG. 3. According to the results shown in FIG. 3, the loaded 5-FU has a significantly higher release rate in alkaline environment compare to neutral (~2 folds) and acidic environment (~4 folds) at 48 hrs. Thus, the nano-carrier of the present invention can serve as an intestine local delivery nano-vehicle to pass through stomach and upper GI tract and then release therapeutic agents (5-FU) in the lower GI tract, thereby being applicable in the per oral chemotherapy for colorectal cancers.

Hence, when the complex of 5-FU and a nano-carrier is applied to treat cancer patients, especially those with colorectal cancers, the 5-FU anticancer drug can be locally released from the complex in lower GI tract and induce cancerous cell cycle arrest.

In Vitro Cancer Cytotoxicity Analysis of the Complex of 5-FU and the Nano-Carrier The colon carcinoma cell line SW480 was purchased from the American Type Culture Collection (ATCC). It was maintained in Leibovitz L-15 medium (PAA Laboratories GmbH, Linz, Austria), supplemented with 10% fetal bovine serum (FBS; GIBCO, Taiwan) and 10%, penicillinstreptomycin (100 μg/mL). Cell line was incubated at 37° C. with 5% $CO_2$ in the air.

The 3-(4,5-dimethylthiazol-2-yl)-2,5-diphenyl tetrazolium bromide (MTT, Sigma Chemical Co., St. Louis, Mo.) assay was performed as described by Mosmann (Mosmann, T. *J. Immunol. Methods* 1983, 65, 55) with slight modifications (Ulukaya, E.; Colakogullari, M.; Wood, E. *J. Chemotherapy* (Basel, Switz.) 2004, 50, 43). SW480 cancer cells were plated in a final concentration of 5000 cells/well and incubated in a tissue culture incubator overnight. 200 μL medium containing drugs at 4 different concentrations of complexes of 5-FU and nano-carriers were placed in a 96-well plate in triplicate and incubated 24 hrs. The culture medium was replaced by 100 μL of fresh medium. MTT was first prepared as a stock solution of 5 mg/mL in PBS. 20 μL of MTT solution was then added to each well. After incubation for an additional 4 hrs at 37° C., 100 μL of SDS solution (10% sodium dodecyl sulfate dissolved in 0.01 N HCl) was added to each well. After centrifugation at 3,220×g for 5 min, the supernatant were transferred to a new 96 well ELISA plate. Absorbance at 490 nm was measured (LP 400 Pasteur Diagnostics) and calculated. Drug-free complete medium was used as the control (blank) and was treated in the same way as the drug-containing media. 5-FU free compound of the same concentration as those loaded on the nano-carriers was applied as the control for the evaluation of the effect of nano-carriers.

Figure 4:
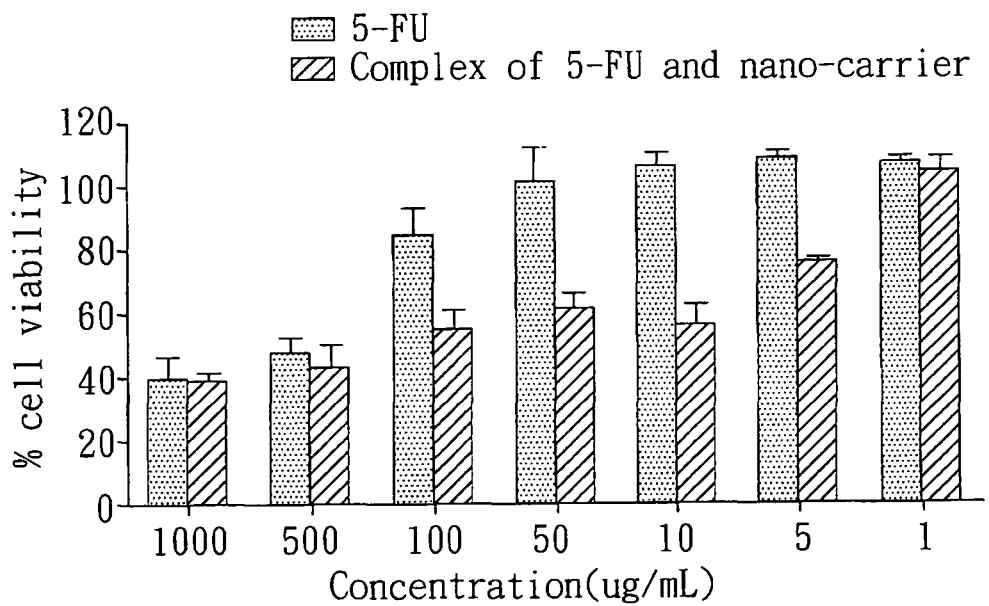
FIG. 4 is a diagram showing the results of the MTT assay of 5-FU and complexes of 5-FU and a nano-carrier of the present invention.

The result of the MTT assay is shown in FIG. 4. According to the results shown in FIG. 4, the complex of 5-FU and the nano-carrier achieves LD (lethal dose) 50% (100 μg/mL) in much lower dosage than 5-FU alone (500 μg/mL). Even at 5 μg/mL of the complex, the therapeutic efficacy still remained 30% in SW480 cancer cell line. Hence, the complex of 5-FU and the nano-carrier of the present invention achieved significantly improved $LD_{50}$ when compounded to the free 5-FU compound.

In conclusion, according to the aforementioned results, a positive association between environmental pH and drug release was observed in PBS, which implied the potential use in the controlled localized drug release in the lower GI tract. In addition, the MTT assay revealed greater dose dependent cytotoxicity to colon cancer cell line than free compounds, and this suggests the potential use of the complex of the anticancer drug and the nano-carrier as the environmental controlled anti-cancer nanocapsule, which is especially suitable for per oral colon cancer chemotherapy.

Although the present invention has been explained in relation to its preferred embodiment, it is to be understood that many other possible modifications and variations can be made without departing from the scope of the invention as hereinafter claimed.

What is claimed is:

1. A nano-carrier with an anticancer drug, comprising:
   a metal nanoparticle; and
   a polynucleotide for connecting the nano-carrier with an anticancer drug having a pyrimidine group, wherein the polynucleotide is connected to a surface of the metal nanoparticie, and the anticancer drug is bound to the polynucleotide through the pyrimidine group, wherein the anticancer drug is Fluorouracil (5-FU), having the formula (I)

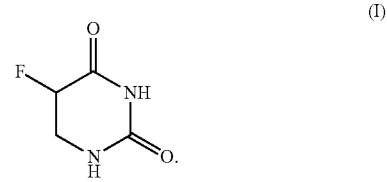

2. The nano-carrier as claimed in claim 1, wherein the metal nanoparticle is an Au nanoparticle, or a nanoparticle coated with an Au shell.

3. The nano-carrier as claimed in claim 1, wherein the diameter of the metal nanoparticle is 1-100 nm.

4. The nano-carrier as claimed in claim 1, wherein the polynucleotide comprises at least one adenine.

5. A nano-carrier with an anticancer drug according to claim 1, wherein the polynucleotide is connected to a surface of the metal nanoparticle through covalent bonding.

6. A nano-carrier with an anticancer drug according to claim 1, wherein the polynucleotide is connected to a surface of the metal nanoparticle through affinity adsorption.

\* \* \* \* \*